(12) United States Patent
Dhurandhar et al.

(10) Patent No.: US 9,346,835 B2
(45) Date of Patent: May 24, 2016

(54) COMPOSITIONS AND METHODS FOR IMPROVING GLUCOSE UPTAKE

(71) Applicant: BOARD OF SUPERVISORS OF LOUISIANA STATE UNIVERSITY AND AGRICULTURAL, Baton Rouge, LA (US)

(72) Inventors: Nikhil V. Dhurandhar, Baton Rouge, LA (US); Bhaskar C. Das, West Nyack, NY (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 0 days.

(21) Appl. No.: 14/434,276

(22) PCT Filed: Oct. 16, 2013

(86) PCT No.: PCT/US2013/065227
§ 371 (c)(1),
(2) Date: Apr. 8, 2015

(87) PCT Pub. No.: WO2014/062794
PCT Pub. Date: Apr. 24, 2014

(65) Prior Publication Data
US 2015/0266903 A1 Sep. 24, 2015

Related U.S. Application Data

(60) Provisional application No. 61/714,899, filed on Oct. 17, 2012.

(51) Int. Cl.
C07F 5/02 (2006.01)
C07F 5/04 (2006.01)

(52) U.S. Cl.
CPC ... *C07F 5/04* (2013.01); *C07F 5/02* (2013.01); *C07F 5/025* (2013.01)

(58) Field of Classification Search
CPC ............... C07F 5/02; C07F 5/025; C07F 5/04
See application file for complete search history.

(56) References Cited

FOREIGN PATENT DOCUMENTS

WO WO2012/112670 8/2012

OTHER PUBLICATIONS

Glodzik et al. "Reduced glucose uptake and Ab in brain regions with hyperintensities in connected white matter" NeuroImage, 2014, vol. 100. pp. 684-691.*
Das et al., "Design and Synthesis of α-aminonitrile-funcationalized Novel Retinoids," Tetrahedron Letters, 50:5670-5672 (2009).
International Search Report dated Jan. 15, 2014 from corresponding PCT Application No. PCT/US2013/065227.

\* cited by examiner

*Primary Examiner* — Joseph Kosack
(74) *Attorney, Agent, or Firm* — McDermott Will & Emery LLP (57) ABSTRACT

A compound includes the structure of general Formula (II), pharmaceutically acceptable salts thereof, and/or solvates thereof: wherein $R^1$, $R^2$, $R^3$, are independently selected from the group consisting of null, hydroxy, alkoxy, and halo, or $R^1$ and $R^2$ taken together form a cyclic boronate ester and $R^3$ is null; wherein when four bonds to boron are present, boron bears a formal negative charge and the structure further comprises a countercation that is potassium or sodium, $X^1$, $X^2$, $X^3$, and $X^4$ are independently selected from the group consisting of O, CH, and N, with the proviso that no more than two of combined O and N are selected, and Z is selected from the group consisting of hydrogen, alkyl, aryl, heteroaryl, and halogen, any of which may be optionally substituted. Such compounds can increase glucose uptake by cells and preferably do not substantially increase adipogenesis.

3 Claims, 2 Drawing Sheets

COMPOSITIONS AND METHODS FOR IMPROVING GLUCOSE UPTAKE

RELATED APPLICATIONS

This application is the U.S. National Stage of International Application No. PCT/US2013/065227, filed Oct. 16, 2013, published in English, and claims the benefit of U.S. Patent Aplication No. 61/714,899 filed on Oct. 17, 2012, the entire teaching of which is incorporated herein by reference.

BACKGROUND OF THE INVENTION

As the epidemic of obesity continues unabated, infectobesity, obesity of infectious origin, has been receiving increasing attention in the recent years (Rossner S., Lakartidningen. 102(24-25):1896-8 (2005); Astrup A., et al., Int J Obes Relat Metab Disord., 22(4):375-6 (1998); Powledge T M., Lancet Infect Dis., 4(10):599 (2004)). Although many factors contribute to the etiology of obesity, a subset of obesity may be caused by infections. In the last two decades, 10 obesity-promoting pathogens have been reported (Dhurandhar N V, et al., Genetics and Hormones, 20(3): 33-39 (2004)). The first human virus, adenovirus type 36 (Ad-36), was reported that caused obesity in experimentally infected animals (Dhurandhar N V, et al., Int J Obesity, 24: 989-996 (2000); Dhurandhar N V, et al., Int J Obesity, 25:990-996 (2001); Dhurandhar N V, et al., J Nutrition, 132:3155-3160 (2002)) and showed association with human obesity (Atkinson R L, et al., International Journal of Obesity, 29:281-286 (2005)). In-vitro experiments have shown that Ad-36 infection of rat preadipocytes (3T3-L1) and human preadipocytes promote their proliferation and differentiation (Vangipuram S D, et al., Obesity Research, 12:770-777 (2004)).

Ad-36 stimulates preadipocytes (pre-fat cells) to differentiate into adipocytes (fat cells), and increases the number of fat cells and their lipid content (Id.). Ad-36 can induce differentiation of preadipocytes even in absence of conventional differentiation inducers such as the cocktail of methyl isobutyl xanthine, dexamethasone, and insulin (MDI). A similar effect of the virus is observed in human adipose derived stem cells (Id.). Rats infected with Ad-36 showed greater adiposity but paradoxically lower insulin resistance 7 months post-infection (Pasarica M, et al., Obesity Research, 12 (supplement):A122 (2004)). Moreover, fat cells from uninfected rats when infected with Ad-36 show increased glucose uptake, indicating greater insulin sensitivity (Dhurandhar N V, et al., Obesity Research, 11:A38 (2003)).

Factors required for increased insulin sensitivity include greater preadipocyte number and differentiation, and activation of cAMP and insulin signaling pathway enzymes (e.g., phosphotidyl inositol-3 kinase (PI3K or PI3 kinase)). Preadiopcyte differentiation in turn is modulated by activation of PI3 kinase and cAMP signaling pathways (Hansen J B, et al., J Biol Chem. 276(5):3175-82 (2001); Reusch J E, et al., Mol Cell Biol. 20(3):1008-20 (2000); Chiou G Y, et al., J Cell Biochem. 94(3):627-34 (2005); Cornelius P, et al., J Cell Physiol. 146(2):298-308 (1991); Burgering B M, et al., Nature 376(6541):599-602 (1995); Magun R, et al., Endocrinology 137(8):3590-3 (1996)). Ad-36 has been shown to increase preadipocyte replication, the number of differentiated adipocytes, and PI3 kinase pathway (Pasarica M, et al., FASEB J 19(4):A70 (2005)).

The liver has a predominate role in fat metabolism and normally accumulates lipids (fat), but only to "normal levels." Excessive lipid accumulation in hepatocytes results in hepatic steatosis, which is metabolically harmful and can result from a variety of liver dysfunctions, such as decreased beta-oxidation or decreased secretion of lipoproteins. Another of the many functions of the liver is to release glucose into circulation. In healthy individuals, liver cells release glucose regularly to regulate blood glucose levels. In contrast, in individuals with diabetes, liver cells release glucose uncontrollably, which increases blood glucose levels. Therefore, reducing glucose release from liver cells (hepatocytes) can be very effective in controlling diabetes.

Excessive lipid accumulation in the liver may contribute to insulin resistance, a condition in which insulin has decreased effectiveness lowering blood sugar, and thus poor glycemic control. Adiponectin, a protein secreted by fat tissue (adipose tissue) improves insulin sensitivity in many ways. Adiponectin acts via adiponectin receptors AdipoR1 and AdipoR2 in the liver to activate AMPK and PPARα pathways (Heiker, J. T. et al. Biol. Chem. 391:1005-1018 (2010)), to decrease systemic and hepatic insulin resistance, and to attenuate liver inflammation and fibrosis (Heiker et al.). It is a strong determinant of hepatic lipid content, as indicated by mice models of adiponectin "knock-out" or overexpression (Nawrocki, A. R. et al. J. Biol. Chem. 281:2654-2660 (2006); Kim, J Y et al. J. Clin. Invest. 117:2621-2637 (2007)). Adiponectin is thought to lower hepatic steatosis by the up-regulation of AMPK-mediated hepatic lipid oxidation (Xu, A. et al. J. Clin. Invest. 112:91-100 (2003)).

Non-alcoholic fatty liver disease (NAFLD) affects up to 20% of adults in the U.S., and includes the excessive accumulation of fat in the liver (hepatic steatosis). It is often associated with obesity and insulin resistance (Fabbrini, E. et al. Proc. Natl. Acad. Sci. USA 106:15430-15435 (2009); Deivanayagam, S. et al. Am. J. Clin. Nutr. 88:257-262 (2008)). The prevalence of NAFLD is about 70-80% in adults with type 2 diabetes or obesity (Targher, G. et al. Diabetes Care 30:1212-1218 (2007); Bellentani, S. et al. Dig. Dis.; 28:155-161 (2010); Parekh, S. et al. Gastroenterology 132: 2191-2207 (2007)), 3-10%, in all children, and up to 40-70% in obese children (Bellentani et al.). NAFLD is associated with greater overall and liver-related mortality (Adams, L. A. et al. Gastroenterology; 129:113-121 (2005); Ekstedt, M. et al. Hepatology 44:865-873 (2006)). In addition to steatosis, inflammation and fibrosis can develop and NAFLD may progress to non-alcoholic steato-hepatitis (NASH), cirrhosis, liver failure and hepatocellular carcinoma. While steatosis is potentially reversible, once it progresses to NASH, there are no established treatments, and the few available medications show limited success (Gupta A. K. et al. J Diabetes Complications 2009; Sanyal A. J. et al. N Engl J Med (2010) 362: 1675-1685). Therefore, the timely prevention and/or treatment of hepatic steatosis is critical. However, even for NAFLD, drug treatment has marginal success (Duvnjak M., et al. J Physiol Pharmacol (2009) 60 Suppl 7:57-66), and reducing dietary fat intake and obesity are the mainstay of treatment (Mishra P. et al. Curr Drug Discov Technol (2007) 4:133-140). Despite the obvious health benefits, compliance with lifestyle changes to achieve sustained improvements in diet or obesity has proved challenging for the general population.

While excess adiposity or a high fat (HF)-diet are risk factors for NAFLD, Adenovirus 36 (Ad36) attenuates hepatic steatosis in mice despite a continued HF-diet and without a reduction in visceral or subcutaneous adiposity. Ad36 appears to qualitatively alter the metabolic quality of adipose tissue to attenuate HF-diet induced hepatic steatosis. This change in the metabolic quality of adipose tissue by Ad36 includes greater uptake and reduced release of fatty acids and greater adiponectin secretion (Rogers, P. M. et al. Diabetes (2008) 57:2321-2331; Pasarica M. et al. Stem Cells 2008 26:969-978). The thiazolidinedione (TZDs) class of drugs can also improve metabolic quality of adipose tissue, up-regulate adiponectin, and improve hepatic steatosis (Nawrocki, A. R. et al. J Biol Chem (2006) 281:2654-2660; Lutchman G. et al. Clin Gastroenterol Hepatol (2006) 4:1048-1052; Shen, Z. et al. Am J Physiol Gastrointest Liver Physiol (2010) 298:G364-374). However, serious side effects of TZDs have been reported (Habib, Z. A. et al. J Clin Endocrinol Metab (2010) 95:592-600; Ramos-Nino, M. E. et al. BMC Med (2007); 5:17; Lipscombe, L. L. et al. JAMA (2007) 298; 2634-2643).

Ad36 does not cause morbidity or unintended mortality in animals. In addition, Ad36 appears to have distinct advantages over the action of the TZDs, particularly in the presence of a HF-diet. Unlike the TZDs, Ad36 does not increase adiposity in HF-fed mice (Fernandes-Santos, C. et al. Pancreas (2009) 38:e80-86; Fernandes-Santos, C. et al. Nutrition (2009) 25:818-827). In the presence of a HF-diet, TZDs can improve glycemic control, but they concurrently promote lipid storage in various organs, including the liver (Fernandes-Santos, C. et al. Pancreas (2009) 38:e80-86; Todd, M. K et al. Am J Physiol Endocrinol Metab (2007) 292:E485-493; Kuda, O et al. J Physiol Pharmacol (2009) 60:135-140). This and other side effects limit the clinical utility of TZDs.

Harnessing certain properties of viruses for beneficial purposes has been creatively used for several years, including the use of bactericidal properties of a bacteriophage virus (Hanlon, G. W. Int J Antimicrob Agents (2007) 30:118-128), the oncolytic ability of a mutant adenovirus (Bischoff, J. R. et al. Science (1996) 274:373-376), or the use of Herpes simplex virus and several other viruses for the treatment of cancers (Crompton, A. M et al. Curr Cancer Drug Targets (2007) 7:133-139), alone, or with various synergistic drugs (Pan, Q. et al. Mol Cell Biochem (2007, 304 (1-2):315-323); Libertini, S. et al. Endocrinology 2007, 148(11):5186-5194).

Therefore, a need exists for agents that improve glucose uptake and preferably do not increase adiposity.

SUMMARY OF THE INVENTION

In some aspects, embodiments disclosed herein relate to compounds and pharmaceutical compositions comprising structures of general Formula I, pharmaceutically acceptable salts thereof, and/or solvates thereof:

I wherein $Ar^1$ is selected from the group consisting of 6-membered aryl and 6-membered heteroaryl, each of which is optionally substituted, $Ar^2$ is selected from the group consisting of 5-membered aryl and 5-membered heteroaryl, each of which is optionally substituted; $R^1$ and $R^2$ are independently selected from the group consisting of hydroxy, alkoxy, and halo, and $R^3$ is selected from the group consisting of null, hydroxy, alkoxy, and halo, or $R^1$ and $R^2$ taken together with the boron atom form a cyclic boronate ester and $R^3$ is null. When four bonds to boron are present (i.e., $R^3$ is not null), boron bears a formal negative charge and the structure further comprises a counter cation, such as potassium, sodium, mercury, or lithium.

In some aspects, embodiments disclosed herein relate to compounds and pharmaceutical compositions comprising structures of general Formula II, pharmaceutically acceptable salts thereof, and/or solvates thereof:

II wherein $R^1$, $R^2$, and $R^3$ are as defined in Formula I;
the ring atoms at $X^1$, $X^2$, $X^3$, and $X^4$ are independently selected from the group consisting of O, C, and N, with the proviso that no more than two of $X^1$, $X^2$, $X^3$, and $X^4$ are O or N; and
Z is selected from the group consisting of null, alkyl, aryl, heteroaryl, and halogen, any of which may be optionally substituted. It will be appreciated by those skilled in the art that any carbon atom at $X^1$, $X^2$, $X^3$, and $X^4$ that is not bonded to the group Z will be bonded to hydrogen.

In certain preferred compounds of Formula II, $R^1$, $R^2$, and $R^3$ are each a halogen, or $R^1$ and $R^2$ taken together with the boron atom form a cyclic boronate ester and $R^3$ is null. In these preferred compounds, the five membered ring comprising $X^1$, $X^2$, $X^3$, and $X^4$ can be an isoxazolyl or furanyl, and Z is null, lower alkyl or phenyl, wherein the lower alkyl and phenyl may be substituted with one or more halogen, hydroxy or combinations thereof In some aspects, embodiments disclosed herein relate to methods to treat diseases selected from the group consisting of hyperglycemia, insulin resistance, prediabetes, diabetes type 1, diabetes type 2, Alzheimer's disease, hepatic steatosis, NAFLD, non-alcoholic steato-hepatitis (NASH), liver dysfunction (e.g., liver dysfunction characterized by fatty liver and/or insulin resistance) and combinations thereof, comprising administering to a subject in need thereof a therapeutically effective amount of a compound of Formula I, pharmaceutically acceptable salts thereof, and/or solvates thereof, optionally with a pharmaceutically acceptable vehicle.

In some aspects, embodiments disclosed herein relate to methods to treat diseases selected from the group consisting of hyperglycemia, insulin resistance, prediabetes, diabetes type 1, diabetes type 2, Alzheimer's disease, hepatic steatosis, NAFLD, non-alcoholic steato-hepatitis (NASH), liver dysfunction (e.g., liver dysfunction characterized by fatty liver and/or insulin resistance) and combinations thereof, comprising administering to a subject in need thereof a therapeutically effective amount of a compound of Formula II, pharmaceutically acceptable salts thereof, and/or solvates thereof, optionally with a pharmaceutically acceptable vehicle.

DETAILED DESCRIPTION OF THE INVENTION

The present disclosure is directed, in part, to compounds that improve glucose uptake, and preferably do not substantially increase adiposity (e.g., less than 5% increase in adiposity), pharmaceutical compositions comprising the compounds and methods of treating diseases disclosed herein by administering the compounds or pharmaceutical compositions.

Ad36 improves glycemic control and has been shown to reduce liver fat in animals. Despite these benefits, it is impractical to use Ad36 infection to improve diabetes in humans. The E4orf1 protein of Ad36 adenovirus has been indicated to be necessary and sufficient for Ad36-induced increased cellular glucose uptake. Ad-36 E4 orf 1 protein has been shown to increase insulin sensitivity and promote preadipocyte differentiation. This protein can be used to increase insulin sensitivity and ameliorate diabetes. E4orf1 is not a secreted protein, thus it needs to be delivered to cells via a delivery system. (See WO2007/064836 and WO2012/006512, incorporated herein, in their entirety). As disclosed herein, chemical analogs that are able to mimic desirable activities of E4orf1 have been developed, and can be used to increase insulin sensitivity and ameliorate diabetes.

In accordance with embodiments disclosed herein, E4orf1 was utilized as a template to design compounds of Formulas I and II. The approach employed was to develop small molecules that mimic the action of E4orf1 protein. Compounds of Formulas I and II were designed as small molecule surrogates of E4orf1 protein based on the cellular action of E4orf1, its molecular partners, and various cell signaling pathways involved in the action of E4orf1.

In one aspect, the compound is of general Formula I, pharmaceutically acceptable salts thereof, and/or solvates thereof:

I wherein $Ar^1$ is selected from the group consisting of 6-membered aryl and 6-membered heteroaryl, each of which is optionally substituted, $Ar^2$ is selected from the group consisting of 5-membered aryl and 5-membered heteroaryl, each of which is optionally substituted; $R^1$ and $R^2$ are independently selected from the group consisting of hydroxy, alkoxy, and halo, and $R^3$ is selected from the group consisting of null, hydroxy, alkoxy, and halo, or $R^1$ and $R^2$ taken together with the boron atom form a cyclic boronate ester and $R^3$ is null. When four bonds to boron are present (i.e., $R^3$ is not null), boron bears a formal negative charge and the structure further comprises a countercation, such as potassium, sodium, mercury or lithium.

In other aspects, the compound is of general Formula II, pharmaceutically acceptable salts thereof, and/or solvates thereof:

II wherein $R^1$, $R^2$, and $R^3$ are as defined in Formula I;

the ring atoms at $X^1$, $X^2$, $X^3$, and $X^4$ are independently selected from the group consisting of O, C, and N, with the proviso that no more than two of $X^1$, $X^2$, $X^3$, and $X^4$ are O or N; and Z is selected from the group consisting of null, alkyl, aryl, heteroaryl, and halogen, any of which may be optionally substituted. It will be appreciated by those skilled in the art that any carbon atom at $X^1$, $X^2$, $X^3$, and $X^4$ that is not bonded to the group Z will be bonded to hydrogen.

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

Although the chemical terms used herein are intended to have their ordinary meaning as recognized by those skilled in the art, the following terms are provided for guidance.

The term "alkyl," as used herein, alone or in combination, refers to a straight-chain or branched-chain alkyl group containing from 1 to 20 carbon atoms. In certain embodiments, the alkyl group may comprise from 1 to 10 carbon atoms. In further embodiments, the alkyl group may comprise from 1 to 6 carbon atoms. Alkyl groups may be optionally substituted as defined herein. Examples of alkyl groups include methyl, ethyl, n-propyl, isopropyl, n-butyl, isobutyl, sec-butyl, tert-butyl, pentyl, iso-amyl, hexyl, octyl, noyl and the like. The term "alkylene," as used herein, alone or in combination, refers to a saturated aliphatic group derived from a straight or branched chain saturated hydrocarbon attached at two or more positions, such as methylene (—$CH_2$—). Unless otherwise specified, the term "alkyl" may include "alkylene" groups.

The term "aryl," as used herein, alone or in combination, means a carbocyclic aromatic system containing one, two or three rings wherein such polycyclic ring systems are fused together. The term "aryl" embraces aromatic groups such as phenyl, naphthyl, anthracenyl, and phenanthryl.

The term "halo," or "halogen," as used herein, alone or in combination, refers to fluorine, chlorine, bromine, or iodine.

The term "heteroaryl," as used herein, alone or in combination, refers to a 3 to 7 membered unsaturated heteromonocyclic ring, or a fused monocyclic, bicyclic, or tricyclic ring system in which at least one of the fused rings is aromatic, which contains at least one atom selected from the group consisting of O, S, and N. In certain embodiments, the heteroaryl may comprise from 5 to 7 carbon atoms. The term also embraces fused polycyclic groups wherein heterocyclic rings are fused with aryl rings, wherein heteroaryl rings are fused with other heteroaryl rings, wherein heteroaryl rings are fused with heterocycloalkyl rings, or wherein heteroaryl rings are fused with cycloalkyl rings. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzidolyl, phenanthrolinyl, dibenzofuranyl, acridinyl, phenanthridinyl, xanthenyl and the like. In particular embodiments, a heteroaryl group may be limited to possessing two heteroatoms total wherein the heteroatoms are selected from O and N.

The term "lower," as used herein, alone or in a combination, where not otherwise specifically defined, means containing from 1 to and including 6 carbon atoms.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that the group is absent.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, $N_3$, SH, $SCH_3$, $C(O)CH_3$, $CO_2CH_3$, $CO_2H$, pyridinyl, thiophene, furanyl, lower carbamate, halophenyl, hydroxyphenyl, haloalkyl, hydroxyalkyl, and lower urea. Two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —$CH_2CH_3$), fully substituted (e.g., —$CF_2CF_3$), monosubstituted (e.g., —$CH_2CH_2F$) or substituted at a level anywhere in-between fully substituted and monosubstituted (e.g., —$CH_2CF_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

Asymmetric centers exist in the compounds disclosed herein. For example, in Formulas I and II, the aminonitrile center comprises a stereogenic carbon, i.e. a carbon bearing four different substituents. These centers may be designated by the symbols "R" or "S," depending on the configuration of substituents around the chiral carbon atom. It should be understood that the invention encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, compounds may exist as tautomers; all tautomeric isomers are provided by this invention. Additionally, the compounds disclosed herein can exist in unsolvated as well as solvated forms with pharmaceutically acceptable solvents such as water, ethanol, and the like. In general, the solvated forms are considered equivalent to the unsolvated forms.

The term "disease" as used herein is intended to be generally synonymous, and is used interchangeably with, the terms "disorder" and "condition" (as in medical condition), in that all reflect an abnormal condition of a subject, the subject being, for example, a human or animal body or of one of its parts that impairs normal functioning, is typically manifested by distinguishing signs and symptoms, and causes the human or animal to have a reduced duration or quality of life.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

The term "inhibition" (and by extension, "inhibitor") as used herein encompasses all forms of functional protein (enzyme, kinase, receptor, channel, etc., for example) inhibition, including neutral antagonism, inverse agonism, competitive inhibition, and non-competitive inhibition (such as allosteric inhibition) Inhibition may be phrased in terms of an $IC_{50}$, defined below.

The term "therapeutically acceptable" refers to those compounds (or salts, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

As used herein, reference to "treatment" of a subject is intended to include prophylaxis.

The term "subject" means all mammals including humans. Examples of subjects include, without limitation, humans, cows, dogs, cats, goats, sheep, pigs, and rabbits. In some embodiments, the subject is a human.

The term "prodrug" refers to a compound that is made more active in vivo. Certain compounds disclosed herein may also exist as prodrugs, as described in Hydrolysis in Drug and Prodrug Metabolism: Chemistry, Biochemistry, and Enzymology (Testa, Bernard and Mayer, Joachim M. Wiley-VHCA, Zurich, Switzerland 2003). Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound.

The compounds disclosed herein can exist as therapeutically acceptable salts. The present invention includes compounds listed above in the form of salts, including acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable. For a more complete discussion of the preparation and selection of salts, refer to Pharmaceutical Salts: Properties, Selection, and Use (Stahl, P. Heinrich. Wiley-VCHA, Zurich, Switzerland, 2002).

The term "therapeutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present invention contemplates sodium, potassium, magnesium, and calcium salts of the compounds disclosed herein, and the like.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N-dibenzylethylenediamine Other representative organic amines useful for the formation of base addition salts include ethylenediamine, ethanolamine, diethanolamine, piperidine, and piperazine.

While it may be possible for the compounds disclosed herein to be administered as the raw chemical, it is also possible to administer them as a pharmaceutical formulation (or composition). Accordingly, provided herein are pharmaceutical formulations which comprise one or more of the compounds disclosed herein, or one or more pharmaceutically acceptable salts, esters, prodrugs, amides, or solvates thereof, together with one or more pharmaceutically acceptable carriers thereof and optionally one or more other therapeutic ingredients. The carrier(s) are compatible with the other ingredients of the formulation and not deleterious to the recipient thereof. The precise formulation selected will be dependent upon the route of administration chosen and other factors. Any of the well-known techniques, carriers, and excipients may be used as suitable and as understood in the art; e.g., in Remington's Pharmaceutical Sciences. The pharmaceutical compositions disclosed herein may be manufactured in any manner known in the art, e.g., by means of conventional mixing, dissolving, granulating, dragee-making, levigating, emulsifying, encapsulating, entrapping or compression processes.

The compounds disclosed herein can be administered in various modes, e.g. orally, topically, or by injection.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual, ocular, and intraocular) administration although the most suitable route may depend upon for example the condition and disorder of the recipient. The formulations may conveniently be presented in unit dosage form and may be prepared by any of the methods well known in the art of pharmacy. Typically, these methods include the step of bringing into association compounds disclosed herein or a pharmaceutically acceptable salt, ester, amide, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the compounds disclosed herein suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, capsules (e.g., push-fit capsules made of gelatin, as well as soft, sealed capsules made of gelatin and a plasticizer, such as glycerol or sorbitol) and the like. Tablets may be made by compression or molding, optionally with one or more accessory ingredients. Compressed tablets may be prepared by compressing in a suitable machine the active ingredient e.g., in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Examples of fillers or diluents for use in oral pharmaceutical compositions such as capsules and tablets include, without limitation, lactose, mannitol, xylitol, dextrose, sucrose, sorbitol, compressible sugar, microcrystalline cellulose (MCC), powdered cellulose, cornstarch, pregelatinized starch, dextrates, dextran, dextrin, dextrose, maltodextrin, calcium carbonate, dibasic calcium phosphate, tribasic calcium phosphate, calcium sulfate, magnesium carbonate, magnesium oxide, poloxamers such as polyethylene oxide, and hydroxypropyl methyl cellulose. Fillers may have complexed solvent molecules, such as in the case where the lactose used is lactose monohydrate. Fillers may also be proprietary, such in the case of the filler PROSOLV® (available from JRS Pharma). PROSOLV® is a proprietary, optionally high-density, silicified microcrystalline cellulose composed of 98% microcrystalline cellulose and 2% colloidal silicon dioxide. Silicification of the microcrystalline cellulose is achieved by a patented process, resulting in an intimate association between the colloidal silicon dioxide and microcrystalline cellulose. PROSOLV® comes in different grades based on particle size, and is a white or almost white, fine or granular powder, practically insoluble in water, acetone, ethanol, toluene and dilute acids and in a 50 g/L solution of sodium hydroxide.

Examples of disintegrants for use in oral pharmaceutical compositions such as capsules and tablets include, without limitation, sodium starch glycolate, sodium carboxymethyl cellulose, calcium carboxymethyl cellulose, croscarmellose sodium, povidone, crospovidone (polyvinylpolypyrrolidone), methyl cellulose, microcrystalline cellulose, powdered cellulose, low-substituted hydroxy propyl cellulose, starch, pregelatinized starch, and sodium alginate.

Additionally, glidants and lubricants may be used in oral pharmaceutical compositions to ensure an even blend of excipients upon mixing. Examples of lubricants include, without limitation, calcium stearate, glyceryl monostearate, glyceryl palmitostearate, hydrogenated vegetable oil, light mineral oil, magnesium stearate, mineral oil, polyethylene glycol, sodium benzoate, sodium lauryl sulfate, sodium stearyl fumarate, stearic acid, talc, and zinc stearate. Examples of glidants include, without limitation, silicon dioxide ($SiO_2$), talc cornstarch, and poloxamers. Poloxamers (or LUTROL®, available from the BASF Corporation) are A-B-A block copolymers in which the A segment is a hydrophilic polyethylene glycol homopolymer and the B segment is hydrophobic polypropylene glycol homopolymer.

Examples of tablet binders include, without limitation, acacia, alginic acid, carbomer, carboxymethyl cellulose sodium, dextrin, ethylcellulose, gelatin, guar gum, hydrogenated vegetable oil, hydroxyethyl cellulose, hydroxypropyl cellulose, hydroxypropylmethyl cellulose, copolyvidone, methyl cellulose, liquid glucose, maltodextrin, polymethacrylates, povidone, pregelatinized starch, sodium alginate, starch, sucrose, tragacanth, and zein.

The compounds disclosed herein may be formulated for parenteral administration by injection, e.g., by bolus injection or continuous infusion. Formulations for injection may be presented in unit dosage form, e.g., in ampoules or in multi-dose containers, with an added preservative. The pharmaceutical compositions may take forms as suspensions, solutions or emulsions in oily or aqueous vehicles, and may contain formulatory agents such as suspending, stabilizing and/or dispersing agents. The pharmaceutical compositions may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the pharmaceutical compositions described above, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the pharmaceutical compositions may take the form of tablets, lozenges, pastilles, or gels formulated in conventional manner. Such compositions may comprise the active ingredient in a flavored basis such as sucrose and acacia or tragacanth.

The compounds disclosed herein may also be formulated in rectal compositions such as suppositories or retention enemas, e.g., containing conventional suppository bases such as cocoa butter, polyethylene glycol, or other glycerides.

In some embodiments, compounds disclosed herein may be administered topically, that is by non-systemic administration. This includes the application of a compound disclosed herein externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Pharmaceutical compositions suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient for topical administration may comprise, for example, from 0.001% to 10% w/w (by weight) of the formulation. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 1% w/w of the formulation.

Topical ophthalmic, otic, and nasal formulations of the present invention may comprise excipients in addition to the active ingredient. Excipients commonly used in such formulations include, but are not limited to, tonicity agents, preservatives, chelating agents, buffering agents, and surfactants. Other excipients comprise solubilizing agents, stabilizing agents, comfort-enhancing agents, polymers, emollients, pH-adjusting agents and/or lubricants. Any of a variety of excipients may be used in formulations of the present invention including water, mixtures of water and water-miscible solvents, such as C1-C7-alkanols, vegetable oils or mineral oils comprising from 0.5 to 5% non-toxic water-soluble polymers, natural products, such as alginates, pectins, tragacanth, karaya gum, guar gum, xanthan gum, carrageenin, agar and acacia, starch derivatives, such as starch acetate and hydroxypropyl starch, and also other synthetic products such as polyvinyl alcohol, polyvinylpyrrolidone, polyvinyl methyl ether, polyethylene oxide, preferably cross-linked polyacrylic acid and mixtures of those products. The concentration of the excipient is, typically, from 1 to 100,000 times the concentration of the active ingredient. In preferred embodiments, the excipients to be included in the formulations are typically selected on the basis of their inertness towards the active ingredient component of the formulations.

Relative to ophthalmic, otic, and nasal formulations, suitable tonicity-adjusting agents include, but are not limited to, mannitol, sodium chloride, glycerin, sorbitol and the like. Suitable buffering agents include, but are not limited to, phosphates, borates, acetates and the like. Suitable surfactants include, but are not limited to, ionic and nonionic surfactants (though nonionic surfactants are preferred), RLM 100, POE 20 cetylstearyl ethers such as PROCOL® CS20 and poloxamers such as PLURONIC® F68.

The pharmaceutical compositions set forth herein may comprise one or more preservatives. Examples of such preservatives include p-hydroxybenzoic acid ester, sodium perborate, sodium chlorite, alcohols such as chlorobutanol, benzyl alcohol or phenyl ethanol, guanidine derivatives such as polyhexamethylene biguanide, sodium perborate, polyquaternium-1, amino alcohols such as AMP-95, or sorbic acid. In certain embodiments, the formulation may be self-preserved so that no preservation agent is required.

For ophthalmic, otic, or nasal administration, the formulation may be a solution, a suspension, or a gel. In some embodiments, the pharmaceutical compositions are for topical application to the eye, nose, or ear in aqueous solution in the form of drops. The term "aqueous" typically denotes an aqueous formulation wherein the formulation is >50%, more preferably >75% and in particular >90% by weight water. These drops may be delivered from a single dose ampoule which may preferably be sterile and thus render bacteriostatic components of the formulation unnecessary. Alternatively, the drops may be delivered from a multi-dose bottle which may preferably comprise a device which extracts any preservative from the formulation as it is delivered, such devices being known in the art.

Compositions of the present invention that are adapted for topical administration to the eye may be isotonic, or slightly hypotonic in order to combat any hypertonicity of tears caused by evaporation and/or disease. This may require a tonicity agent to bring the osmolality of the formulation to a level at or near 210-320 milliosmoles per kilogram (mOsm/kg). The formulations of the present invention generally have an osmolality in the range of 220-320 mOsm/kg, and preferably have an osmolality in the range of 235-300 mOsm/kg. The ophthalmic formulations will generally be formulated as sterile aqueous solutions.

In certain ophthalmic embodiments, the compositions of the present invention are formulated with one or more tear substitutes. A variety of tear substitutes are known in the art and include, but are not limited to: monomeric polyols, such as, glycerol, propylene glycol, and ethylene glycol; polymeric polyols such as polyethylene glycol; cellulose esters such hydroxypropylmethyl cellulose, carboxy methylcellulose sodium and hydroxy propylcellulose; dextrans such as dextran 70; vinyl polymers, such as polyvinyl alcohol; and carbomers, such as carbomer 934P, carbomer 941, carbomer 940 and carbomer 974P. Certain formulations of the present invention may be used with contact lenses or other ophthalmic products.

In some embodiments, pharmaceutical compositions are prepared using a buffering system that maintains the formulation at a pH of about 4.5 to a pH of about 8, for example, a pH in a range from about 7 to about 8.

In particular embodiments, a pharmaceutical composition of the present invention is administered once a day. However, the compositions may also be formulated for administration at any frequency of administration, including once a week, once every 5 days, once every 3 days, once every 2 days, twice a day, three times a day, four times a day, five times a day, six times a day, eight times a day, every hour, or any greater frequency. Such dosing frequency is also maintained for a varying duration of time depending on the therapeutic regimen. The duration of a particular therapeutic regimen may vary from one-time dosing to a regimen that extends for months or years. The formulations may be administered at varying dosages, but typical dosages are one to two drops at each administration, or a comparable amount of a gel or other formulation. One of ordinary skill in the art would be familiar with determining a therapeutic regimen for a specific indication.

Gels for topical or transdermal administration may comprise, generally, a mixture of volatile solvents, nonvolatile solvents, and water. In certain embodiments, the volatile solvent component of the buffered solvent system may include lower (C1-C6) alkyl alcohols, lower alkyl glycols and lower glycol polymers. In further embodiments, the volatile solvent is ethanol. The volatile solvent component is thought to act as a penetration enhancer, while also producing a cooling effect on the skin as it evaporates. The nonvolatile solvent portion of the buffered solvent system is selected from lower alkylene glycols and lower glycol polymers. In certain embodiments, propylene glycol is used. The nonvolatile solvent slows the evaporation of the volatile solvent and reduces the vapor pressure of the buffered solvent system. The amount of this nonvolatile solvent component, as with the volatile solvent, is determined by the pharmaceutical compound or drug being used. When too little of the nonvolatile solvent is in the system, the pharmaceutical compound may crystallize due to evaporation of volatile solvent, while an excess may result in a lack of bioavailability due to poor release of drug from solvent mixture. The buffer component of the buffered solvent system may be selected from any buffer commonly used in the art; in certain embodiments, water is used. A common ratio of ingredients is about 20% of the nonvolatile solvent, about 40% of the volatile solvent, and about 40% water. There are several optional ingredients which can be added to the topical composition. These include, but are not limited to, chelators and gelling agents. Appropriate gelling agents can include, but are not limited to, semisynthetic cellulose derivatives (such as hydroxypropylmethylcellulose) and synthetic polymers, galactomannan polymers (such as guar and derivatives thereof) and cosmetic agents.

Lotions include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives or a fatty acid such as stearic or oleic acid together with an alcohol such as propylene glycol or a macrogel. The formulation may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin, may also be included.

Drops may comprise sterile aqueous or oily solutions or suspensions and may be prepared by dissolving the active ingredient in a suitable aqueous solution of a bactericidal and/or fungicidal agent and/or any other suitable preservative, and, in certain embodiments, including a surface active agent. The resulting solution may then be clarified by filtration, transferred to a suitable container which is then sealed and sterilized by autoclaving or maintaining at 98-100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Formulations for topical administration in the mouth, for example buccally or sublingually, include lozenges comprising the active ingredient in a flavored basis such as sucrose and acacia or tragacanth, and pastilles comprising the active ingredient in a basis such as gelatin and glycerin or sucrose and acacia.

For administration by inhalation, compounds may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the invention may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Preferred unit dosage formulations are those containing an effective dose or an appropriate fraction thereof, of the active ingredient.

It should be understood that in addition to the ingredients particularly mentioned above, the pharmaceutical compositions described above may include other agents conventional in the art having regard to the type of formulation in question, for example those suitable for oral administration may include flavoring agents.

A therapeutically effective amount of a compound of Formula I or Formula II is administered to a subject to treat disease. A therapeutically effective amount is an amount sufficient to produce the intended effect under the conditions of administration. For example, an amount that is sufficient to improve glucose uptake, improve glycemic control and/or to improve liver function can be administered. The appropriate dosages can be determined by a clinician of ordinary skill using methods known in the art, which take into consideration the individual's age, sensitivity to drugs, tolerance to drugs, severity of disease and overall well-being, as well as other factors. Suitable dosages can be from about 0.1-about 500.0 mg/kg body weight per treatment.

The compounds disclosed herein can be administered by any appropriate mode, for example orally, parenterally (including subcutaneous, intradermal, intramuscular, intravenous, intraarticular, and intramedullary), intraperitoneally, transmucosally, transdermally, rectally a topically (including dermal, buccal, sublingual, ocular, and intraocular). Administration can be of systemic or topical activity as indicated.

In certain instances, it may be appropriate to administer at least one of the compounds described herein (or a pharmaceutically acceptable salt, ester, or prodrug thereof) in combination with another therapeutic agent. When a compound of Formula I or II is administered with another therapeutic agent, they compound can be administered before, substantially at the same time as or after the other therapeutic agent. In general, the compound the other therapeutic agent are administered to provide substantial overlap of their respective therapeutic effects. By way of example only, in a treatment for diabetes involving administration of one of the compounds described herein, increased therapeutic benefit may result by also providing the patient with another therapeutic agent for diabetes. In any case, regardless of the disease, disorder or condition being treated, the overall benefit experienced by the patient may simply be additive of the two therapeutic agents or the patient may experience a synergistic benefit.

Non-limiting examples of possible combination therapies include use of certain compounds disclosed herein with biologics of E4orf1.

Thus, in another aspect, certain embodiments provide methods for treating disease or disorders comprising administering to a subject a therapeutically effective amount of a compound of Formula I or II, optionally with another therapeutic agent. The disease or disorder to be treated in accordance with the invention can be hyperglycemia, insulin resistance, prediabetes, diabetes type 1, diabetes type 2, hepatic steatosis, NAFLD, non-alcoholic steato-hepatitis (NASH), and liver dysfunction (e.g., liver dysfunction characterized by fatty liver and/or insulin resistance), metabolic syndrome, polycystic ovary syndrome (PCOS). Advantageously, treatment of these diseases with a compound of Formula I or II does not increase adiposity in the subject.

In some embodiments, the invention is a method of treating diabetes comprising administering to an subject in need thereof a therapeutically effective amount of a compound of Formula I or II. Advantageously, the method can be used to treat diabetes without substantially increasing adipogenesis in the subject.

In some embodiments, the invention is a method of treating hyperglycemia, insulin resistance associated with PCOS, metabolic syndrome, Alzheimer's disease, and/or prediabetes, comprising administering to an subject in need thereof a therapeutically effective amount of a compound of Formula I or II. Advantageously, the method can be used to treat hyperglycemia, insulin resistance associated with PCOS, metabolic syndrome, Alzheimer's disease and/or prediabetes without substantially increasing adipogenesis in the subject.

In some embodiments, the invention is a method of treating liver dysfunction (e.g., liver dysfunction characterized by fatty liver and/or insulin resistance) comprising administering to an subject in need thereof a therapeutically effective amount of a compound of Formula I or II. Advantageously, the method can be used to treat liver dysfunction (e.g., liver dysfunction characterized by fatty liver and/or insulin resistance) without substantially increasing adipogenesis in the subject.

In some embodiments, the invention is a method of treating hepatic steatosis comprising administering to an subject in need thereof a therapeutically effective amount of a compound of Formula I or II. Advantageously, the method can be used to treat hepatic steatosis without substantially increasing adipogenesis in the subject.

In some embodiments, the invention is a method of treating NAFLD comprising administering to an subject in need thereof a therapeutically effective amount of a compound of Formula I or II. Advantageously, the method can be used to treat NAFLD without substantially increasing adipogenesis in the subject.

In some embodiments, the invention is a method of treating NASH comprising administering to an subject in need thereof a therapeutically effective amount of a compound of Formula I or II. Advantageously, the method can be used to treat NASH without substantially increasing adipogenesis in the subject.

It is understood that modifications which do not substantially affect the activity of the various embodiments of this invention are also included within the definition of the invention provided herein. Accordingly, the following examples are intended to illustrate but not limit the present invention.

EXAMPLES

Materials and Methods: All reagents were purchased from commercial sources and used without treatment, unless otherwise indicated. The products were purified by column chromatography over silica gel. $^1$H NMR and $^{13}$C NMR spectra were recorded at 25° C. at 300 MHz and 75 MHz, respectively, with TMS as internal standard. Abbreviations for signal coupling are as follows: s, singlet; d, doublet; t, triplet; q, quartet; m, multiplet; br, broad. Column chromatography was performed using $SiO_2$ (0.040-0.063 mm, 230-400 mesh ASTM) from Merck. All reagents were obtained from commercial sources. Mass spectra were recorded on Varian MS mass spectrometer.

In designing compounds of Formulas I and II, the protein sequence was determined in-silico, and the active site of E4orf1 protein of Ad36 virus was modeled with ICM software (Halgren, T. A. Merck molecular force field 0.1. Basis, form, scope, parameterization, and performance of MMFF94. Journal of Computational Chemistry 1996, 17, 490-519; Totrov, M.; Abagyan, R. Flexible protein-ligand docking by global energy optimization in internal coordinates. Proteins 1997, 215-220) and the active site of the protein was generated. After generating active site of protein in-silico, a small library of chemical compounds was screened. After identifying these compounds in-silico, exemplary molecules 1-5 were synthesized based on transformations disclosed herein. A common motif in the compounds disclosed herein is the alpha-aminonitrile pharmacophore and all compounds are substituted with amino groups containing boronic acids/boronic acid derivatives. The compounds disclosed herein are water soluble, hydrophobic, and possess a log P values under therapeutic index (3-5-4.5) Amino nitriles derivatives may be used as precursors of protein synthesis. Using this process, compounds 1-5 below were designed and prepared.

1

[5-(4-Fluoro-phenyl)-isoxazol-3-yl]-[4-(4,4,5,5-tetramethyl-[1,3,2]dioxaborolan-2-yl)-phenylamino]-acetonitirile

2

(5-Phenyl-isoxazol-3-yl)-[4-(4,4,5,5-tetramethyl-[1,3,2]dioxaborolan-2-yl)-phenylamino]-acetonitrile -continued

(5-Methyl-isoxazol-3-yl)-[4-(4,4,5,5-tetramethyl-[1,3,2]dixaborolane-2-yl)-phenylamino]-acetonitrile Potassium-(4-trifluorolboranyl-phenylamino)-[5-(4-fluoro-phenyl)-isoxazol-3-yl]-acetonitrile salt

Potasium-(4-trifluoroboranyl-phenylamino)-furan-2-yl-acetonitirile salt

Compounds were synthesized according to Scheme 1 using the following general procedure. To a 10 mL round bottomed flask containing aldehyde A (0.5 mmol, 1.0 eq), amine B (0.5 mmol, 1.0 eq), TMSCN (trimethylsilyl cyanide) (0.6 mmol, 1.2 eq) and water (2 mL) was added InCl₃ (indium chloride) (0.05 mmol, 10 mol %) as the catalyst. The resulting mixture was stirred at room temperature overnight. After the reaction was completed, the crude solid product was filtered and washed by water, hexane and further purified by a silica gel chromatography using ethylacetate and hexanes as solvent. All compounds were characterized by using proton and carbon nuclear magnetic resonance spectroscopy (NMR) and high resolution mass spectrometry (HRMS).

Scheme 1

-continued

1, R = 4-fluoro phenyl

2, R = Phenyl

3, R = Methyl ($CH_3$)

In Scheme 2 below, compounds 4 and 5 were synthesizes as potassium salt of trifluoroborate of boronic ester to make compounds more water soluble. Compound C (0.052 mmol) was dissolved in methanol (MeOH) (1 mL). To the above solvent 4.5 M $KF_2H$ solution (0.21 mmol, 47 mL) was added. The reaction mixture was stirred at room temperature for two hours. Next, the solvent was removed under in vacuo. Hot acetone was added and the solvent was removed under vacuum. The resulting white solid was washed with ethylacetate (3×5 mL) to provide pure solid products 4 and 5 in good yields. The two compounds were characterized by proton and carbon NMR and HRMS.

Scheme 2

4, R = 4-fluoro phenyl

5, R = Furyl,

Testing of E4orf1 Mimetics 1-5: For the following screens, compounds 1-5 were dissolved in DMSO. 3T3-L1 pre adipocytes were first exposed to different concentrations (5 μM, 10 μM, 20 μM, 50 μM and 100 μM) of the compounds to test for toxicity compared with DMSO control exposure. Concentrations of 50 μM and 100 μM showed extreme toxicity and cell death at Day2 of exposure, as indicated in Table 1 below. Exposure to other concentrations was followed until Day5. Compound 2 was the most toxic at 20 μM on Day 5.

TABLE 1

Cell toxicity of compounds at various doses.

| | Day 1 | Day 2 | Day 3 | Day 4 | Day 5 |
|---|---|---|---|---|---|
| 5 μM | | | | | |
| DMSO | 0% | 0-5% | 0-5% | 0-5% | 0-5% |
| 1 | 0% | 0-5% | 0-5% | 0-5% | ≥5% |
| 2 | 0% | 0-5% | 0-5% | 10-20% | 10-20% |
| 3 | 0% | 0-5% | 0-5% | 0-5% | 0-5% |
| 4 | 0% | 0-5% | 0-5% | 0-5% | 0-5% |
| 5 | 0% | 0-5% | 0-5% | 0-5% | 0-5% |
| 10 μM | | | | | |
| DMSO | 0-5% | 0-5% | 0-5% | 0-5% | 0-5% |
| 1 | 5-10% | 5-10% | 5-10% | 5-10% | 5-10% |
| 2 | 5-10% | >10% | ≥10% | 30-40% | ≥40% |
| 3 | 0-5% | >5% | ≥10% | ≥10% | ≥10% |
| 4 | 0-5% | >5% | ≥10% | ≥10% | ≥10% |
| 5 | 0-5% | >5% | ≥10% | ≥10% | ≥10% |
| 20 μM | | | | | |
| DMSO | 0-5% | ≥5% | ≥5% | ≥5% | ≥5% |
| 1 | 5-10% | ≥10% | ≥10% | 10-15% | 10-15% |
| 2 | >10% | 20-30% | 40-50% | 60-70% | 70-80% |
| 3 | 5-10% | 15-20% | ≥20% | 20-30% | ≥30% |
| 4 | 5-10% | 10-15% | ≥15% | ≥15% | ≥15% |
| 5 | 5-10% | 10-15% | 10-15% | 10-15% | 10-15% |
| 50 μM | | | | | |
| DMSO | 0-5% | 10-15% | | | |
| 1 | 30-40% | 90-95% | | | |
| 2 | 30-40% | 95-100% | | | |
| 3 | 15-20% | 90-95% | | | |
| 4 | 30-40% | 90-95% | | | |
| 5 | >15% | 90-95% | | | |
| 100 μM | | | | | |
| DMSO | 30-40% | 30-40% | | | |
| 1 | >90% | 95-100% | | | |
| 2 | >90% | 95-100% | | | |
| 3 | 60-70% | 95-100% | | | |
| 4 | >90% | 95-100% | | | |
| 5 | >90% | 95-100% | | | |

Figure 1:
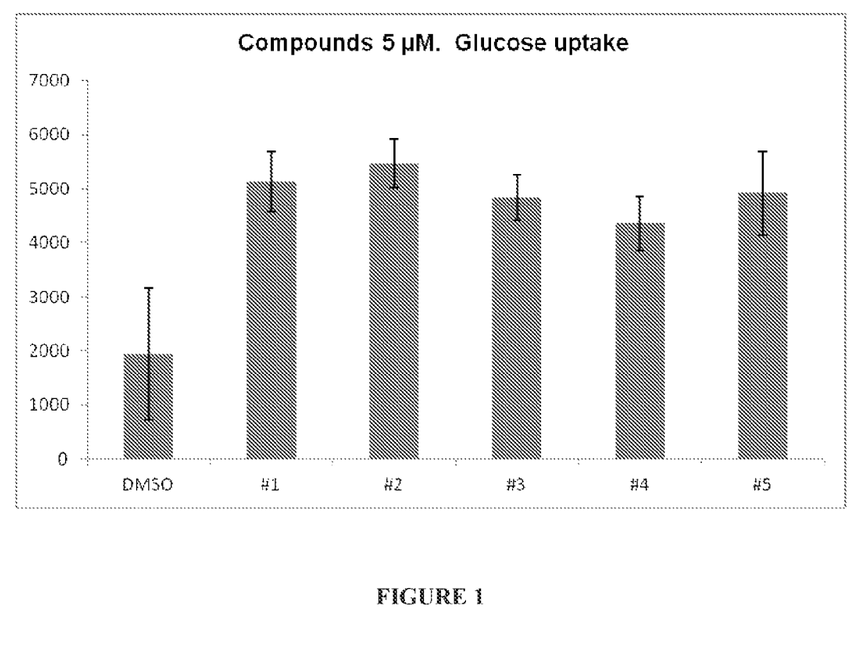
FIG. 1 is a graph showing that exemplary compounds 1-5 all increased basal glucose uptake in 3T3-L1 cells.
Figure 2:
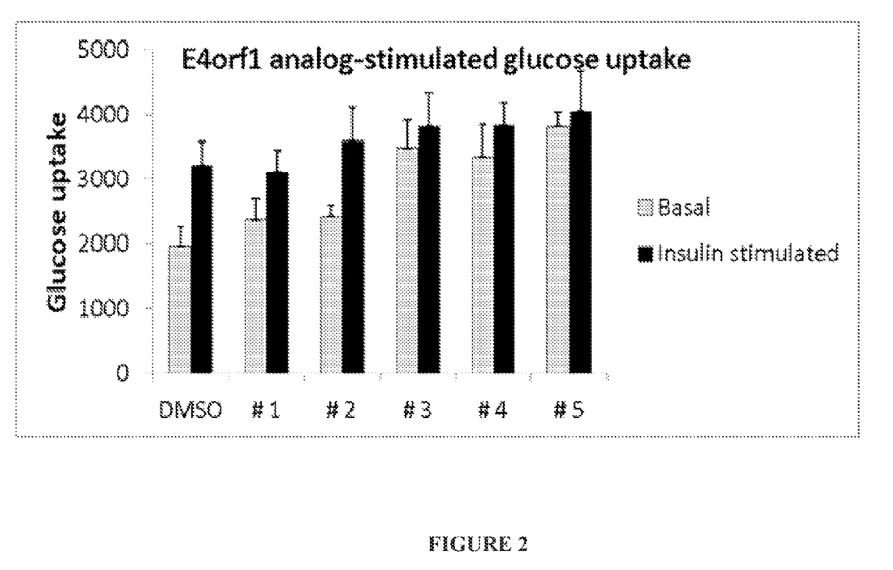
FIG. 2 is a graph showing that exemplary compounds 1-5 increased basal and insulin stimulated glucose uptake.

Next, glucose uptake by 3T3-L1 cells exposed to compounds 1-5 was determined at 5 μM concentration. Cells were exposed to compounds 1-5 for 24 hours and exposure to DMSO was used as the control group. 2-Deoxy glucose (2-DG) uptake was determined using the analog compounds without serum starving the cells prior to determining glucose uptake. As indicated in FIG. 1 glucose uptake in 3T3-L1 pre-adipocytes was determined by exposing cells to compounds 1-5 for 24 hours without serum starvation. All compounds show significant increase (p<0.05) in glucose uptake under basal conditions compared with the DMSO treated control cells. To confirm these observations glucose uptake was examined under basal and insulin stimulated conditions with cells exposed to compounds 1-5 for 24 hours. As seen in FIG. 2, increased glucose uptake was observed in cells exposed to compounds 1-5 with 3, 4 and 5 showing the most significant increase.

Throughout this application various publications have been referenced within parentheses. The disclosures of these publications in their entireties are hereby incorporated by reference in this application in order to more fully describe the state of the art to which this invention pertains.

Although the invention has been described with reference to the disclosed embodiments, those skilled in the art will readily appreciate that the specific examples and studies detailed above are only illustrative of the invention. It should be understood that various modifications can be made without departing from the spirit of the invention. Accordingly, the invention is limited only by the following claims.

What is claimed is:

1. A compound comprising the structure of general Formula II, pharmaceutically acceptable salts thereof, and/or solvates thereof:

II wherein $R^1$ and $R^2$ are independently selected from the group consisting of hydroxy, alkoxy, and halo, and $R^3$ is selected from the group consisting of null, hydroxy, alkoxy, and halo, or $R^1$ and $R^2$ taken together with the boron atom form a cyclic boronate ester and $R^3$ is null, wherein when four bonds to boron are present, boron bears a formal negative charge and the structure further comprises a countercation selected from the group consisting of potassium and sodium;

the ring atoms at $X^1$, $X^2$, $X^3$, and $X^4$ are independently selected from the group consisting of O, C, and N, with the proviso that no more than two of $X^1$, $X^2$, $X^3$, and $X^4$ are O or N; and Z is selected from the group consisting of null, alkyl, aryl, heteroaryl, and halogen, any of which may be optionally substituted and any carbon atom at $X^1$, $X^2$, $X^3$, and $X^4$ that is not bonded to the group Z is bonded to hydrogen.

2. The compound of claim 1, comprising a structure selected from the group consisting of:

1

2

3

-continued and pharmaceutically acceptable salts and/or solvates thereof.

3. A pharmaceutical composition comprising a compound of claim 1 and a pharmaceutically acceptable vehicle.

* * * * *